(12) United States Patent
Druesne et al.

(10) Patent No.: US 8,198,065 B2
(45) Date of Patent: Jun. 12, 2012

(54) MUTANT STRAINS OF LACTIC ACID BACTERIA HAVING A NON-PHOSPHORYLABLE LACTOSE PERMEASE

(75) Inventors: Anne Druesne, Bures sur Yvette (FR); Peggy Garault, Montlhéry (FR); Jean-Michel Faurie, Jouy-en-Josas (FR); Nadine Licau, Les Ulis (FR)

(73) Assignee: Compagnie Gervais Danone, Paris (FR)

( * ) Notice: Subject to any disclaimer, the term of this patent is extended or adjusted under 35 U.S.C. 154(b) by 1079 days.

(21) Appl. No.: 11/915,964

(22) PCT Filed: May 30, 2006

(86) PCT No.: PCT/EP2006/062715
§ 371 (c)(1),
(2), (4) Date: Feb. 4, 2008

(87) PCT Pub. No.: WO2006/128864
PCT Pub. Date: Dec. 7, 2006

(65) Prior Publication Data
US 2009/0238921 A1 Sep. 24, 2009

(30) Foreign Application Priority Data
May 31, 2005 (FR) ...................................... 05 05497

(51) Int. Cl.
*C12N 1/21* (2006.01)

(52) U.S. Cl. ..................................... 435/252.3; 435/471
(58) Field of Classification Search .................. None
See application file for complete search history.

(56) References Cited

U.S. PATENT DOCUMENTS
5,382,438 A * 1/1995 Hottinger et al. ............... 426/43
5,639,648 A   6/1997 Mainzer et al.

OTHER PUBLICATIONS

Stahl et al,.Journal of Bacteriology .1984, vol. 158, No. 2, p. 411-418).*
Henner et al., Journal of Bacteriology .1988, vol. 170, p. 5102-5109).*
International Search Report for PCT/EP2006/062715 filed May 30, 2006.
Gunnewijk M G et al: "Phosphorylation state of HPr determines the level of expression and the extent of phosphorylation of the lactose transport protein of *Streptococcus thermophilus*"; The Journal of Biological Chemistry; Nov. 3, 2000; vol. 275, No. 44, pp. 34073-34079; XP002348522.
Poolman B et al: "Lactose transport system of *Streptococcus thermophilus*, The role of histidine residues"; The Journal of Biological Chemistry; May 5, 1992; pp. 9150-9157; XP002348523.

* cited by examiner

*Primary Examiner* — Irene Marx
(74) *Attorney, Agent, or Firm* — Alston & Bird LLP

(57) ABSTRACT

The invention concerns lactic acid bacteria strains wherein the phosphorylable histidine of the IIA domain of lactose permease is replaced by a non-phosphorylable amino acid. Said strains have a reduced post-acidification and are useful in particular for preparing fermented dairy products.

3 Claims, 6 Drawing Sheets

```
> I-2967                                                      TCCACAACCTCTTG   14
>I-3213   CTTCCAATAATCTTGACTGCAGCTGAACTCTTCTTCATTCCACAACCTCTTG  52

>I-2967   TGTTCCTTGTTGTCTTTATGATTATCTCTGACTCAGTAGAATATGGTCAATG   66
>I-3213   TGTTCCTTGTTGTCTTTATGATTATCTCTGACTCAGTAGAATATGGTCAATG  104

>I-2967GAAAACGGGACACCGTGATGAATCACTTACTTTGTCAGTTCGTCCACTTATT  118
>I-3213 GAAAACGGGACACCGTGATGAATCACTTACTTTGTCAGTTCGTCCACTTATT  156

>I-2967   GATAAACTTGGTGGTGCGATGTCAAACTGGCTTGTTTCTACATTTGCCGTAG  170
>I-3213   GATAAACTTGGTGGTGCGATGTCAAACTGGCTTGTTTCTACATTTGCCGTAG  208

>I-2967   CTGCCGGTATGACAACAGGTGCCTCAGCATCAACAATTACAACACATCAACA  222
>I-3213   CTGCCGGTATGACAACAGGTGCCTCAGCATCAACAATTACAACACATCAACA  260

>I-2967   GTTTATCTTTAAGCTTGGCATGTTTGCTTTCCCAGCAGCAACAATGCTTATC  274
>I-3213   GTTTATCTTTAAGCTTGGCATGTTTGCTTTCCCAGCAGCAACAATGCTTATC  312

>I-2967   GGTGCCTTCATTGTTGCTCGTAAAATCACTTTGACTGAAGCACGTCACGCTA  326
>I-3213   GGTGCCTTCATTGTTGCTCGTAAAATCACTTTGACTGAAGCACGTCACGCTA  364

>I-2967   AAATTGTTGAAGAATTGGAACATCGCTTTAGCGTAGCAACTTCTGAAAATGA  378
>I-3213   AAATTGTTGAAGAATTGGAACATCGCTTTAGCGTAGCAACTTCTGAAAATGA  416

>I-2967   AGTTAAAGCTAACGTCGTATCTCTTGTAACCCCTACAACTGGTTATTTGGTT  430
>I-3213   AGTTAAAGCTAACGTCGTATCTCTTGTAACCCCTACAACTGGTTATTTGGTT  468

>I-2967   GATCTCTCAAGTGTTAATGATGAACACTTTGCTTCAGGTAGCATGGGTAAAG  482
>I-3213   GATCTCTCAAGTGTTAATGATGAACACTTTGCTTCAGGTAGCATGGGTAAAG  520

>I-2967   GTTTCGCCATTAAACCTACTGATGGAGCTGTCTTTGCACCAATTAGTGGTAC  534
>I-3213   GTTTCGCCATTAAACCTACTGATGGAGCTGTCTTTGCACCAATTAGTGGTAC  572

>I-2967   CATTCGTCAAATTCTTCCTACTCGCCATGCAGTTGGTATTGAAAGTGAAGAT  586
>I-3213   CATTCGTCAAATTCTTCCTACTCGCCATGCAGTTGGTATTGAAAGTGAAGAT  624

>I-2967   GGTGTCATTGTTCTTATCCACGTTGGCATCGGAACAGTTAAACTTAATGGTG  638
>I-3213   GGTGTCATTGTTCTTATCGCGGTTGGCATCGGAACAGTTAAACTTAATGGTG  676

>I-2967   AAGGATTCATTAGTTACGTAGAACAAGGTGATCATGTTGAAGTTGGACAAA   689
>I-3213   AAGGATTCATTAGTTACGTAGAACAAGGTGATCATGTTGAAGTTGGACAAA   727

> I-2967   AACTTCTTGAGTTCTGGTCACCAATTATTGAGAAAAATGGTCTTGATGACA  740
>I-3213   AACTTCTTGAGTTCTGGTCACCAATTATTGAGAAAAATGGTCTTGATGACA   778

>I-2967   CAGTACTTGTCACTGTAACTAATTCAGAAAAATTCAGTGCTTTCCATCTTG  791
>I-3213   CAGTACTTGTCACTGTAACTAATTCAGAAAAATTCAGTGCTTTCCATCTTG  829

>I-2967   AACAAAAGTTGGAGAAAAGGTAGAAGCTTTGTCTGAAGTTATTACCTTCAA  843
>I-3213   AACAAAAGTTGGAGAAAAGGTAGAAGCTTTGTCTGAAGTTATTACCTTCAA  881

>I-2967   AAAAGGAGAATAATCTATGAACATGACTGAAAAAATTCAAACTTATTTAAAC  895
>I-3213   AAAAGGAGAATAATCTATGAACATGACTGAAAAAATTCAAACTTATTTAAAC  933

>I-2967   GATCCAAAGATTGTTAGCGTTAATACTGTTGATGCTCACTCAGATCATAAG  946
>I-3213   GATCCAAAGATTGTTAGCGTTAATACTGTTGATGCTCACTCAGATCATAAG  984
```

Figure 1

```
>I-2967   TATTTTGAATCTCTTGAAGAATTTTCTGAAGGGGAGATGAAGTTAAGACAAT    998
>I-3213   TATTTTGAATCTCTTGAAGAATTTTCTGAAGGGGAGATGAAGTTAAGACAAT    1036

>I-2967   CTCTTAATGGAAAATGGAAAATTCACTATGCTCAGAATACAAATCAGGTTTT    1050
>I-3213   CTCTTAATGGAAAATGGAAAATTCACTATGCTCAGAATACAAATCAGGTTTT    1088

>I-2967   AAAAGACTTTTATAAAACAGAATTTGATGAAACTGATTTGAATTTCATCAAT    1102
>I-3213   AAAAGACTTTTATAAAACAGAATTTGATGAAACTGATTTGAATTTCATCAAT    1140

>I-2967   GTACCAGGTCATTTAGAGCTTCAAGGTTTTGGTTCTCCACAATATGTGAATA    1154
>I-3213   GTACCAGGTCATTTAGAGCTTCAAGGTTTTGGTTCTCCACAATATGTGAATA    1192

>I-2967   CCCAATATCCTTGGGATGGTAAAGAATTCCTTCGTCCACCTCAAGTTCCTCA    1206
>I-3213   CCCAATATCCTTGGGATGGTAAAGAATTCCTTCGTCCACCTCAAGTTCCTCA    1244

>I-2967   AGAATCAAATGCTG                                          1220
>I-3213   AGAATCAAATGCTGTTGCATCATACGTTAAACAT                      1278
```

Figure 1 (continued)

```
                        SEQUENCE LISTING

<160> NUMBER OF SEQ ID NOS: 2

<210> SEQ ID NO 1
<211> LENGTH: 1220
<212> TYPE: DNA
<213> ORGANISM: Streptococcus thermophilus
<220> FEATURE:
<221> NAME/KEY: misc_feature
<222> LOCATION: (1)..(1220)
<223> OTHER INFORMATION: Sequence of the lacS gene of the I-2967 parent
      strain

<400> SEQUENCE: 1
tccacaacct cttgtgttcc ttgttgtctt tatgattatc tctgactcag tagaatatgg      60
tcaatggaaa acgggacacc gtgatgaatc acttactttg tcagttcgtc cacttattga     120
taaacttggt ggtgcgatgt caaactggct tgtttctaca tttgccgtag ctgccggtat     180
```

```
gacaacaggt gcctcagcat caacaattac aacacatcaa cagtttatct ttaagcttgg    240
catgtttgct ttcccagcag caacaatgct tatcggtgcc ttcattgttg ctcgtaaaat    300
cactttgact gaagcacgtc acgctaaaat tgttgaagaa ttggaacatc gctttagcgt    360
agcaacttct gaaaatgaag ttaaagctaa cgtcgtatct cttgtaaccc ctacaactgg    420
ttatttggtt gatctctcaa gtgttaatga tgaacacttt gcttcaggta gcatgggtaa    480
aggtttcgcc attaaaccta ctgatggagc tgtctttgca ccaattagtg gtaccattcg    540
tcaaattctt cctactcgcc atgcagttgg tattgaaagt gaagatggtg tcattgttct    600
tatccacgtt ggcatcggaa cagttaaact taatggtgaa ggattcatta gttacgtaga    660
acaaggtgat catgttgaag ttggacaaaa acttcttgag ttctggtcac caattattga    720
gaaaaatggt cttgatgaca cagtacttgt cactgtaact aattcagaaa aattcagtgc    780
tttccatctt gaacaaaaag ttggagaaaa ggtagaagct ttgtctgaag ttattacctt    840
caaaaaagga gaataatcta tgaacatgac tgaaaaaatt caaacttatt taaacgatcc    900
aaagattgtt agcgttaata ctgttgatgc tcactcagat cataagtatt ttgaatctct    960
tgaagaattt tctgaagggg agatgaagtt aagacaatct cttaatgaa aatggaaaat    1020 tcactatgct cagaatacaa atcaggtttt aaaagacttt tataaaacag aatttgatga    1080
aactgatttg aatttcatca atgtaccagg tcatttagag cttcaaggtt ttggttctcc    1140
acaatatgtg aatacccaat atccttggga tggtaaagaa ttccttcgtc cacctcaagt    1200
tcctcaagaa tcaaatgctg                                                1220

<210> SEQ ID NO 2
<211> LENGTH: 1278
<212> TYPE: DNA
<213> ORGANISM: Streptococcus thermophilus
<220> FEATURE:
<221> NAME/KEY: misc_feature
<222> LOCATION: (1)..(1278)
<223> OTHER INFORMATION: Sequence of the lacS gene of the I-3213 variant

<400> SEQUENCE: 2
cttccaataa tcttgactgc agctgaactc ttcttcattc cacaacctct tgtgttcctt     60
gttgtcttta tgattatctc tgactcagta gaatatggtc aatggaaaac gggacaccgt    120
gatgaatcac ttactttgtc agttcgtcca cttattgata aacttggtgg tgcgatgtca    180
aactggcttg tttctacatt tgccgtagct gccggtatga caacaggtgc ctcagcatca    240
acaattacaa cacatcaaca gtttatcttt aagcttggca tgtttgcttt cccagcagca    300
acaatgctta tcggtgcctt cattgttgct cgtaaaatca ctttgactga agcacgtcac    360
gctaaaattg ttgaagaatt ggaacatcgc tttagcgtag caacttctga aaatgaagtt    420
aaagctaacg tcgtatctct tgtaaccct acaactggtt atttggttga tctctcaagt    480
gttaatgatg aacactttgc ttcaggtagc atgggtaaag gtttcgccat taaacctact    540
gatggagctg tctttgcacc aattagtggt accattcgtc aaattcttcc tactcgccat    600
gcagttggta ttgaaagtga agatggtgtc attgttctta tccacgttgg catcggaaca    660
gttaaactta atggtgaagg attcattagt tacgtagaac aaggtgatca tgttgaagtt    720
ggacaaaaac ttcttgagtt ctggtcacca attattgaga aaaatggtct tgatgacaca    780
gtacttgtca ctgtaactaa ttcagaaaaa ttcagtgctt tccatcttga acaaaaagtt    840
ggagaaaagg tagaagcttt gtctgaagtt attaccttca aaaaggaga ataatctatg    900 aacatgactg aaaaaattca aacttattta aacgatccaa agattgttag cgttaatact    960
```

```
gttgatgctc actcagatca taagtatttt gaatctcttg aagaattttc tgaaggggag    1020
atgaagttaa gacaatctct taatggaaaa tggaaaattc actatgctca gaatacaaat    1080
caggttttaa aagactttta taaaacagaa tttgatgaaa ctgatttgaa tttcatcaat    1140
gtaccaggtc atttagagct tcaaggtttt ggttctccac aatatgtgaa tacccaatat    1200
ccttgggatg gtaaagaatt ccttcgtcca cctcaagttc ctcaagaatc aaatgctgtt    1260
gcatcatacg ttaaacat                                                  1278
```

MUTANT STRAINS OF LACTIC ACID BACTERIA HAVING A NON-PHOSPHORYLABLE LACTOSE PERMEASE

CROSS REFERENCE TO RELATED APPLICATIONS

This application is a national stage application filed under 35 USC 371 of International Application No. PCT/EP2006/062715, filed May 30, 2006, which claims priority from French patent application 0505497 filed May 31, 2005.

FIELD AND BACKGROUND OF THE INVENTION

The present invention relates to the field of milk fermentation. More specifically, this invention relates to novel mutants of Streptococcus thermophilus expressing a mutant lactose permease, the lactose transport activity of which is modified. These strains, and ferments comprising them, can be used to obtain fermented dairy products having good conservation properties.

Yogurts are conventionally obtained by fermentation of milk with a combination of various lactic acid bacteria, chosen from strains of Streptococcus thermophilus and of Lactobacillus bulgaricus. During the fermentation, which is carried out at a temperature of approximately 40 to 45° C., these bacteria mainly use lactose as energy substrate, and produce lactic acid which leads to coagulation of the milk; when the pH reaches a value of approximately 4.8 to 4.5, this fermentation step (also known as "acidification") is terminated by cooling the product. The latter is then kept cold during the rest of the manufacturing and packaging process, until its consumption.

However, cooling does not completely stop the lactic fermentation; even when the product is kept at 4° C., a gradual increase in its acidity is observed over time.

This phenomenon, known as post-acidification, is responsible for degradation of the organoleptic qualities of the product during its storage.

Post-acidification results essentially from the use, by the bacteria, of the lactose remaining in the product at the end of the controlled acidification step. In order to prevent it, it has been proposed to use strains of lactic acid bacteria which do not ferment lactose, or ferment it very little.

The enzymes essential for lactose fermentation in Streptococcus thermophilus and Lactobacillus bulgaricus are encoded by the lactose operon, which contains the lacS gene, encoding lactose permease, and the lacZ gene, encoding β-galactosidase. These proteins are respectively responsible for lactose transport and hydrolysis. In order to obtain non-post-acidifying strains of lactic acid bacteria, it has therefore been proposed to produce artificial variants, or to select natural mutants, in which the activity of at least one of these enzymes is affected.

Patent EP 1078074 (the company Gervais Danone) relates to L. bulgaricus mutants deficient in β-galactosidase activity, comprising nonsense mutation in at least one of the genes of the lactose operon. This patent describes more specifically a mutant for which analysis of the sequence reveals two point mutations: one introducing a stop codon into the β-galactosidase gene, which induces the inability of this mutant to use lactose; the other mutation induces an amino acid change in the permease gene (Lys->Asn at position 122); EP 1078074 does not report any affect of this mutation on the phenotype of the mutant.

WO 01/88150 describes mutants of a Lactobacillus strain. These mutants are incapable of using lactose, but conserve the ability to express β-galactosidase. WO 01/88150 does not specify the nature or the position of the mutation in question, and simply indicates that it may be located in one of the structural genes of the lactose operon, for example the permease, or in a regulatory region of the lactose operon, or in a gene involved in controlling the expression of the lactose operon.

The mutants described in the documents mentioned above have in common the property of being completely incapable of using lactose. They can only grow on milk if the latter is supplemented with a sugar other than lactose, generally glucose. The acidification and post-acidification properties of these mutants are controlled by the amount of glucose added.

In order to provide an alternative to these mutants, the inventors have investigated whether it is possible to obtain strains of lactic acid bacteria having, firstly, an ability to use lactose during their growth that is comparable to that of the wild-type strains, and, secondly, a restricted ability to use lactose during the stationary phase, so as to reduce or abolish the post-acidification phenomenon. With this aim, they were interested in the possibility of acting on the regulation of lactose transport into lactic acid bacterial cells, and in particular into S. thermophilus cells.

The transport of extracellular lactose into S. thermophilus cells is carried out by means of lactose permease LacS. This lactose transport is carried out by symport with a proton, or by antiport with the intracellular galactose resulting from the degradation of the lactose.

The lactose transport is dependent on two phenomena: firstly, the phosphorylation state of the lactose permease and, secondly, the expression of the lacS gene encoding this lactose permease. These two aspects are addressed in detail below.

Phosphorylation of Lactose Permease

The LacS protein is composed of a translocation domain and a regulatory domain (IIA). These domains contain various histidine residues, the phosphorylation of which is involved in the regulation of lactose transport. In particular, the IIA domain can be phosphorylated on histidine 552. This phosphorylation is carried out by the HPr protein (histidine-containing phosphocarrier protein), itself phosphorylated beforehand.

HPr can be phosphorylated:
  on a serine by an ATP-dependent protein kinase; the reverse reaction of hydrolysis of HPr(Ser-P) is catalyzed by a phosphatase activity (HPr(Ser-P) phosphatase);
  on a histidine HPr(His~P), with a phosphoryl group originating from phosphoenol pyruvate, and by means of enzyme I (EI).

Only the HPr form phosphorylated on histidine allows phosphorylation of lactose permease on histidine 552.

It has been observed, on an in vitro model of proteoliposomes reconstituting the membrane environment of the LacS protein and its phosphorylation by HPr(His~P), that this phosphorylation has no effect on lactose transport by symport with a proton (Gunnewijk and Poolman, 2000a), but increases by a factor of approximately 2 the flow of lactose/galactose exchange.

Transcription of the lacS Gene

The transcription of the lactose operon is induced by growth in a lactose-containing medium. The promoter of the lacS and Z genes contains a cre (catabolite responsive element) site which allows regulation by CcpA: CcpA represses the expression of lacS and of lacZ. On the other hand, CcpA has an activating effect on transcription of the gene encoding lactate dehydrogenase (van den Bogaard et al., 2000).

The HPr(Ser-P) form is capable of interacting with CcpA. These proteins together will make it possible to form a complex with the cre site, thereby bringing about repression of transcription of the lacS gene (Jones et al., 1997).

It has been observed (Gunnewijk and Poolman, 2000b) that the HPr(Ser-P) form is dominant at the beginning of the exponential growth phase of *S. thermophilus* cultures and decreases over the course of said phase, whereas the HPr (His~P) form appears during the exponential phase and is at a maximum at entry into the stationary phase. The change from HPr(Ser-P) to HPr(His~P) takes place in parallel with the decrease in lactose and the increase in galactose in the culture medium, and with a very large increase in the expression of lactose permease.

Thus, the phosphorylation state of the HPr protein appears to play a role in the regulation of lactose transport, by compensating for the decrease in lactose in the medium, through, firstly, the level of expression of the LacS protein and, secondly, the regulation of its activity.

On the basis of the observations reported above, Gunnewijk and Poolman have proposed the following model: when lactose is abundant in the medium, the expression of the lacS gene is repressed by the HPr(Ser-P)/CcpA complex. During fermentation, the accumulation of galactose in the medium and the decrease in available lactose bring about a decrease in the ability of the bacterium to cause lactose to penetrate (and therefore a decrease in acidification of the medium). This decrease results in a reduction in glycolytic activity, and a decrease in ATP concentration along with an increase in inorganic phosphate concentration, leading to a reduction in the activity of HPr(Ser-P) kinase to the benefit of the activity of HPr(Ser-P) phosphatase, which would have the effect of reducing the concentration of HPr(Ser-P). This reduction in HPr(Ser-P) concentration makes it possible to lift the catabolic repression of the lacS gene and, consequently, to increase the production of lactose permease. In parallel, the increase in HPr(His~P) would make it possible to increase the phosphorylation of lactose permease on histidine 552, and therefore the ability to transport lactose by antiport with galactose.

This model, which suggests that the phosphorylation of lactose permease on histidine 552 by HPr(His~P) increases the flow of lactose in cells when the amount of substrate in the medium decreases, makes it possible to suppose that the acidification at the end of the exponential phase could be slowed down if this phosphorylation was prevented. However, it is based in part on in vitro experiments and does not make it possible to judge in advance the real part played in vivo by the increase in the phosphorylation of lactose permease, relative to the increase in its expression, in lactose importation in vivo. In addition, the observations concerning the effects of the concentration of HPr(Ser-P) and HPr (His~P) on the increase in the expression and in phosphorylation of LacS were made on bacteria in the exponential phase or at the beginning of the stationary phase; no indication is given with regard to the concentrations of these two forms of HPr at more advanced stages of the stationary phase.

The only information available with regard to the effect of the absence of LacS phosphorylation on histidine 552 is given in a publication by Poolman et al. (Poolman et al., 1992), which describes various plasmids containing the sequence encoding the *Streptococcus thermophilus* LacS enzyme, mutated on various histidine residues. These plasmids are used to transform a strain of *E. coli* in which the endogenous lacS gene has been previously deleted. The lactose transport in the strains transformed with the various mutants is evaluated in comparison to that observed in the same strain of *E. coli* containing a plasmid encoding the wild-type LacS enzyme of *Streptococcus thermophilus*. No significant difference is observed with regard to the H552R mutant in which the natural histidine is replaced with an arginine. Poolman et al. attribute this result either to the ineffectiveness of the phosphorylation of the wild-type LacS enzyme of *Streptococcus thermophilus* by *E. coli* HPr(His~P), or to the fact that this phosphorylation does not play a role in lactose transport.

The inventors have, however, investigated whether a mutation preventing the phosphorylation of LacS on the histidine residue could have an effect on the acidification and post-acidification properties of the mutant bacterium.

For this study, they chose an industrial strain of *Streptococcus thermophilus*. This strain, deposited with the CNCM on Dec. 12, 2002, under number I-2967, makes it possible to obtain fermented dairy products having an advantageous texture; however, this strain conduces a considerable post-acidification.

The inventors constructed and characterized a mutant of this strain, expressing, in place of the wild-type lactose permease, a mutated lactose permease that cannot be phosphorylated on histidine 552.

They noticed that this mutant strain had an acidification curve different from that of the parent strain. The acidification begins more slowly in the case of the mutant than in that of the parent strain, and the maximum acidification rate of the mutant is lower. However, an equivalent pH is reached after 6 hours of fermentation for the two strains. It is in terms of the post-acidification that the difference between the two strains is the most marked. Under the same storage conditions (28 days of storage at 10° C.), the ΔpH (difference between the pH at D0 and the pH at D28) is of the order of 0.6 in the case of the parent strain, and of the order of 0.4 in the case of the mutant strain. This difference in post-acidification does not come from a difference in terms of the survival of the bacteria. This is in fact equivalent for the two strains. Furthermore, the fermented products obtained with the mutant have the same texture qualities as those obtained with the parent strain.

SUMMARY OF THE INVENTION

The present invention therefore relates, firstly, to a method for obtaining a mutant lactic acid bacteria strain having a lower post-acidification than the parent strain from which it is derived, characterized in that a mutation of the codon encoding the HPr(His~P)-phosphorylatable histidine of the IIA domain of lactose permease is introduced into the genomic DNA, in particular the chromosomal DNA, of said parent strain, said mutation inducing the replacement of said histidine with a non-phosphorylatable amino acid.

According to a preferred embodiment of the present invention, said strain is a strain of *Streptococcus thermophilus*, and said mutation induces the replacement of the histidine at position 552 of lactose permease with a non-phosphorylatable amino acid.

Said non-phosphorylatable amino acid may be any amino acid, with the exception of serine, tyrosine, histidine and threonine. Alanine will preferably be chosen.

Advantageously, the codon encoding the histidine at position 552 of lactose permease is replaced with the codon encoding an alanine. This mutation generates a BstUI restriction site which facilitates the screening of the mutants obtained.

The method in accordance with the invention can be carried out using conventional techniques of site-directed mutagenesis, in particular PCR mutagenesis, well known to those skilled in the art.

The mutated DNA thus obtained is then inserted into a vector for integration of the gene into the bacterial chromosome. This integration is preferably carried out by recombination of the insert carried by the vector with the homologous region of the bacterial chromosome.

Conventionally, the mutated DNA is inserted into an integrative vector carrying a selectable marker (for example, a gene for resistance to an antibiotic), and this vector is introduced into the bacteria in which it is desired to perform the mutation. Said bacteria are subsequently cultured on a selective medium (for example, if the selectable marker is a gene for resistance to an antibiotic, in the presence of the corresponding antibiotic), and the bacteria which are capable of growing under these conditions, which are those which have integrated the vector by homologous recombination between the insert and the homologous region of the bacterial chromosome, are recovered. The structure integrated into the chromosome consists of the sequences of the vector flanked, firstly, by the mutated sequence originating from the insert and, secondly, by the homologous sequence of the host bacterium.

The bacteria thus selected are cultured on a nonselective medium, in order to allow excision of the sequences originating from the vector, which takes place by homologous recombination between the regions flanking these sequences. Half of the bacteria in which this recombination has taken place contain the "wild-type" sequence originating from the host bacterium, and the other half contain the mutated sequence originating from the insert. The bacteria carrying the mutation are then selected by any appropriate means. For example, if the mutation creates a restriction site, the selection can be carried out on the basis of the presence of this restriction site in a PCR amplification product of the mutant region.

Integrative vectors are available for many lactic acid bacteria. Conventionally, for a given bacterial species, an integrative vector is a vector which can be introduced into the bacteria of this species, but which is incapable of replicating therein.

By way of examples of vectors that can be used as integrative vectors in the *Streptococcus thermophilus* mention will be made of Pgem5, Puc19 (Mollet et al., 1993) and Pnd324 (Duan et al., 1999).

Advantageously, in order to increase the transformation efficiency, a vector which replicates conditionally in the chosen bacterium may be used as integrative vector. In this case, the bacteria into which the vector has been introduced are, firstly, cultured under conditions that are permissive for its replication, which enables it to become established in these transformed bacteria; secondly, the bacteria are cultured under conditions that are nonpermissive for the replication of the vector, and it is possible, as in the case of the conventional integrative vectors, to carry out the selection of the bacteria in which the vector has been integrated into the chromosome.

By way of examples of conditional-replication vectors that can be used as integrative vectors in a large number of lactic acid bacteria, mention will be made of the thermosensitive vectors described by Biswas et al. and Maguin et al. (Biswas et al., 1993; Maguin et al., 1996), and also in PCT application WO 93/18164, or the vectors pwv01 (Law et al., 1995) and Puc122 (Frere et al., 1998).

A subject of the invention is also a lactic acid bacteria strain that can be obtained by means of a method in accordance with the invention.

This strain is characterized in that it contains, in its chromosomal DNA, a mutation of the codon encoding the HPr (His~P)-phosphorylatable histidine of the IIA domain of lactose permease, said mutation inducing the replacement of said histidine with a non-phosphorylatable amino acid.

According to a preferred embodiment of the present invention, said strain is a strain of *Streptococcus thermophilus*, in which the lactose permease gene contains a mutation which induces the replacement of the histidine at position 552 of the protein with a non-phosphorylatable amino acid.

A lactic acid bacteria strain in accordance with the invention was deposited according to the Treaty of Budapest, on May 10, 2004, with the CNCM (Collection Nationale de Culture de Microorganismes) [National Collection of Microorganism Cultures], 25 rue du Docteur Roux, in Paris, under number I-3213. It is a mutant strain of *S. thermophilus*, derived from the CNCM strain I-2967 (deposited with the CNCM on Dec. 12, 2002), by the introduction, by site-directed mutagenesis, of a mutation replacing the histidine 552 codon with an alanine codon.

The lactic acid bacteria strains in accordance with the invention have, during their growth phase, a lactose permease activity similar to that of the parent strain from which they are derived. They therefore have lactose assimilation and acidification capacities comparable to those of the parent strain from which they are derived. On the other hand, the lactose permease activity during the stationary phase is reduced compared with that of the parent strain, which leads to a reduced post-acidification.

Advantageously, the lactic acid bacteria strains in accordance with the invention are derived from lactic acid bacteria having a β-galactosidase activity, and they conserve this activity. They can grow normally on milk not supplemented with a sugar other than lactose.

Preferably, the bacterial strains according to the invention are mutants suitable for the food industry (or food-grade mutants). They are advantageously derived from characterized bacterial strains having advantageous dairy product fermentation properties.

The present invention also relates to a lactic ferment comprising at least one bacterial strain as described above. According to a specific embodiment, a lactic ferment according to the invention comprises at least one mutant strain of *S. thermophilus* expressing a lactose permease in which histidine 552 has been replaced with a non-phosphorylatable residue, combined with at least one other lactic acid bacteria strain, for example a strain of *L. bulgaricus*, that may optionally also have a reduced post-acidification (for example, resulting from the mutation, in accordance with the invention, of lactose permease, or else resulting from a β-galactosidase-inactivating mutation).

A method for preparing a fermented dairy product, comprising a step during which milk is fermented using a lactic ferment as described above, is also an integral part of the present invention, as is any fermented dairy product that can be obtained by means of such a method, such as a yoghurt, a fermented milk, a fermented drink, a kefir, a cheese or a fermented infant milk.

The experimental examples which follow, illustrated by the figures, disclose certain aspects of the present invention in greater detail, without, however, limiting the subject thereof.

BRIEF DESCRIPTION OF THE DRAWINGS

FIG. 1: Comparison of the sequence of the lacS gene of the I-3213 variant with the sequence of the lacS gene of the I-2967 parent strain.

EXAMPLES

Example 1

Production of the Mutant

Figure 2:
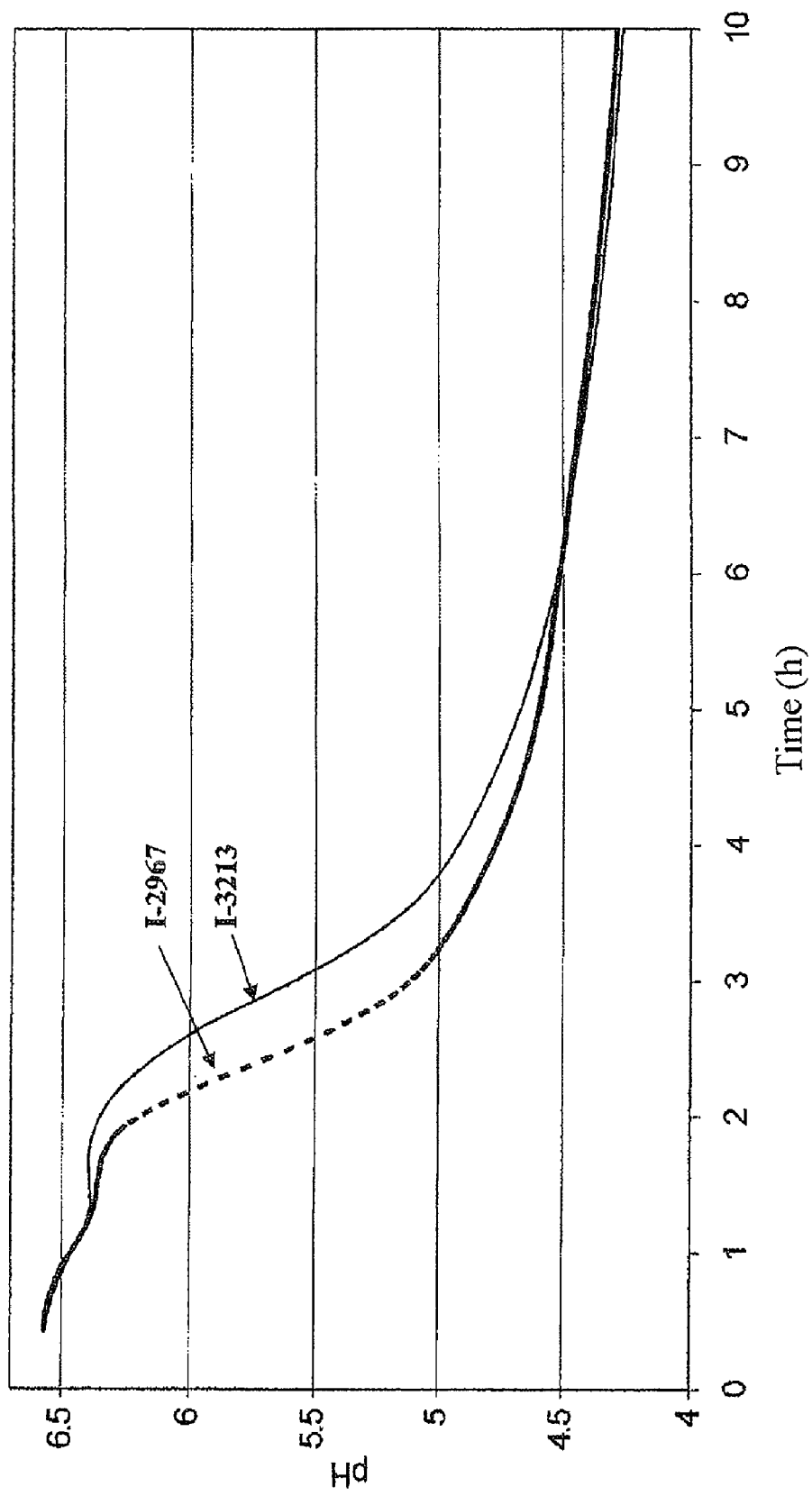
FIG. 2: Comparison of the acidification curves obtained with the I-3213 mutant and the I-2967 parent strain.

The starting strain is the I-2967 *S. thermophilus* strain, deposited with the CNCM on Dec. 12, 2002.

In the sequence of the lacS gene, the codon for histidine 552 (the histidine which is phosphorylatable) was replaced with an alanine codon, by double recombination. In addition, the mutation carried out (replacement of the second nucleotide of codon 552 with a cytosine, instead of an adenine) created a BstU1 restriction site in the gene. This made it possible to select the clones that had integrated the desired mutation into the lacS gene.

The stability of the mutation was verified using one of the clones obtained (deposited with the CNCM on May 10, 2004, under number I-3213), by 6 successive subculturings, followed by sequencing of the LacS gene. FIG. 1 shows the comparison of the sequence of the lacS gene of the I-3213 variant (SEQ ID NO: 2) with that of the lacS gene of the I-2967 parent strain (SEQ ID NO: 1). The mutation is clearly present: the codon for histidine 552 now encodes an alanine. There is no unwanted mutation elsewhere in the lacS gene.

The I-3213 mutant is suitable for agrofood use since it does not contain any residual sequence of the plasmid used to integrate the mutation of the lacS gene.

Example 2

Physiological Tests Carried Out on the I-3213 Mutant

In order to verify that the I-3213 mutant is less post-acidifying than the I-2967 parent strain, products are produced in pure strain and are monitored up until D+28: acidification, post-acidification, survival, texture.

2.A—Protocol

Regeneration of the strains by 2 subculturings.
Preparation of Ferments on Sterile Milk supplemented with yeast extracts, with incubation at 44° C., until an acidity of 85° D is reached (corresponding to $10^8$ to $10^9$ CFU/ml).
Inoculation of a mixture of 120 g of powdered skimmed milk+930 ml of water+1 g N3 gelatin peptone (Organotechnie), pasteurized for 10 min at 95° C., with 1% (v/v) of ferment.
Incubation in jars in an incubator at 44° C., until a pH of 4.65 is reached.
Fermentation arrested by placing the jars in ice-cold water for 30 minutes.
Storage of products for 28 days in a cold store at 10° C.

2.B—Monitoring—Comparison of the Acidification by the Mutants Compared With the I-2967 Strain 2.B.1. Acidification Curves Using the CINAC system (Acidification Kinetics, Alliance Instruments), the pH is continuously measured over time. It is thus possible to obtain:
the acidification curve of each strain,
the first time derivative, which gives the acidification rate.

2.B.2. Measurement of the pH

The change in pH during storage of the products is monitored using an MP220 pH meter from Mettler Toledo.

2.B.3. Measurement of the Dornic Acidity

The measurement of the Dornic acidity (D°) makes it possible to titer the molar concentration of $H_3O^+$ ions. The number in degrees Dornic corresponds to the number of tenths of milliliters of sodium hydroxide solution at the concentration of 0.1 N which are required to neutralize 10.32 g of milk. Neutrality is visualized using a colored indicator, phenolphthalein. Around the region where it changes color (pH 8.2), phenolphthalein goes from colorless to pink. One degree Dornic represents 100 mg of lactic acid per liter of milk.

2.B.4. Preparation of the Mix for the Tests Produced

The milk medium is reconstituted from 120 g of powdered skimmed milk (Milex 240, Arla Food Ingredients)+930 ml of deionized water+1 g of N3 peptide (Vital Armor 950, Armor Proteins). The mix is mixed until complete homogenization. The medium is then rehydrated for 30 min at ambient temperature, and then pasteurized at 95° C. for 10 minutes.

2.B.5. Strain Survival

The survival measurements are carried out on a sucrose-containing M17 agar medium. Surface isolation via a spiral plater (WASP from AES). Incubation at 37° C. under $H_2CO_2$. Reading after incubation for 72 hours.

The pure-strain acidification curves were produced in duplicate.

2.B.6. Interpretation

Figure 3:
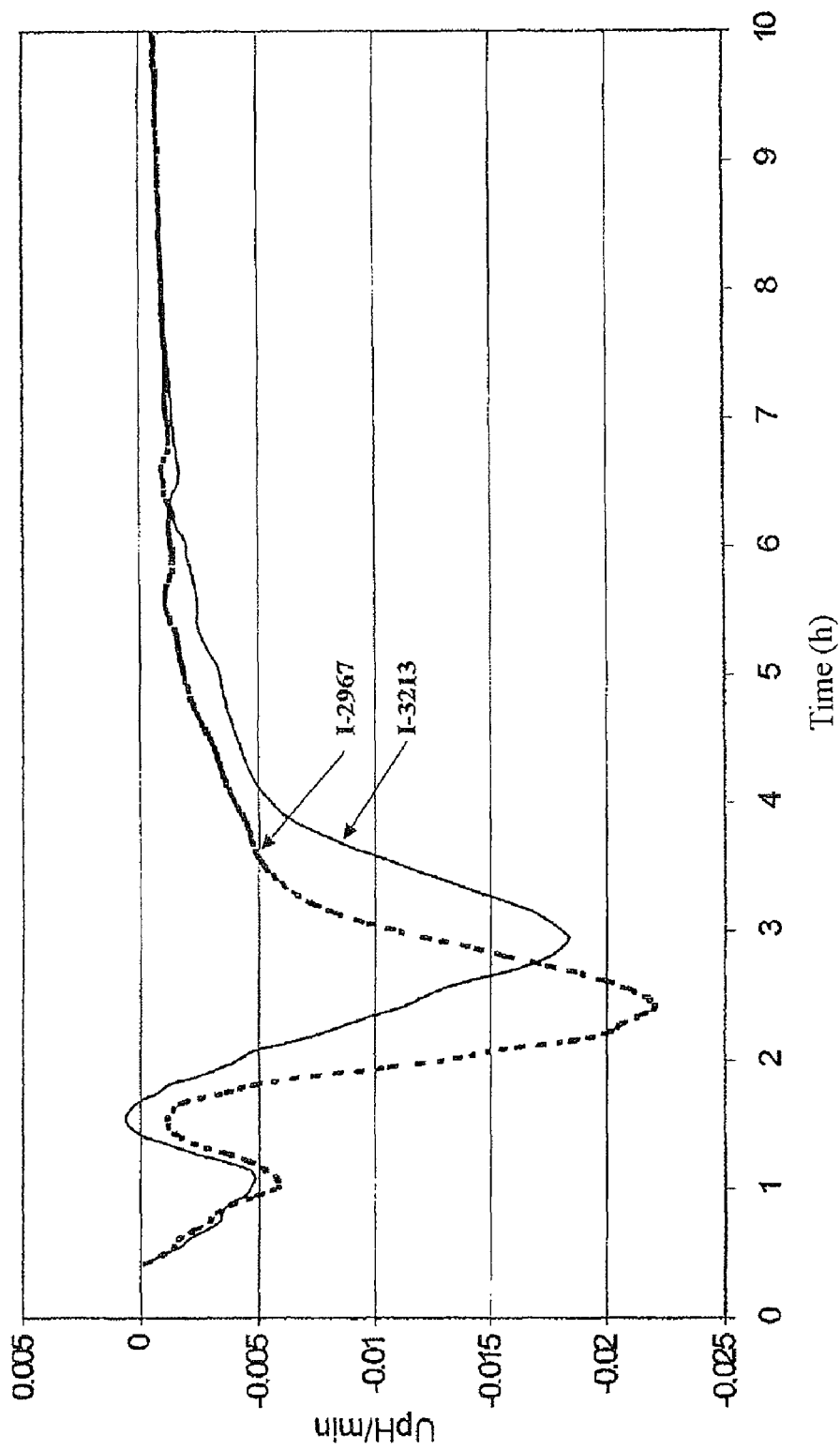
FIG. 3: Comparison of the acidification rates of the I-3213 mutant and of the I-2967 parent strain.

The results, given in FIGS. 2 and 3, show that the I-3213 mutant has a slower acidification curve than the parent strain, with a more pronounced urea effect and a lower maximum acidification rate. However, the pH 4.50 is reached in 6 hours for the two strains.

Figure 4:
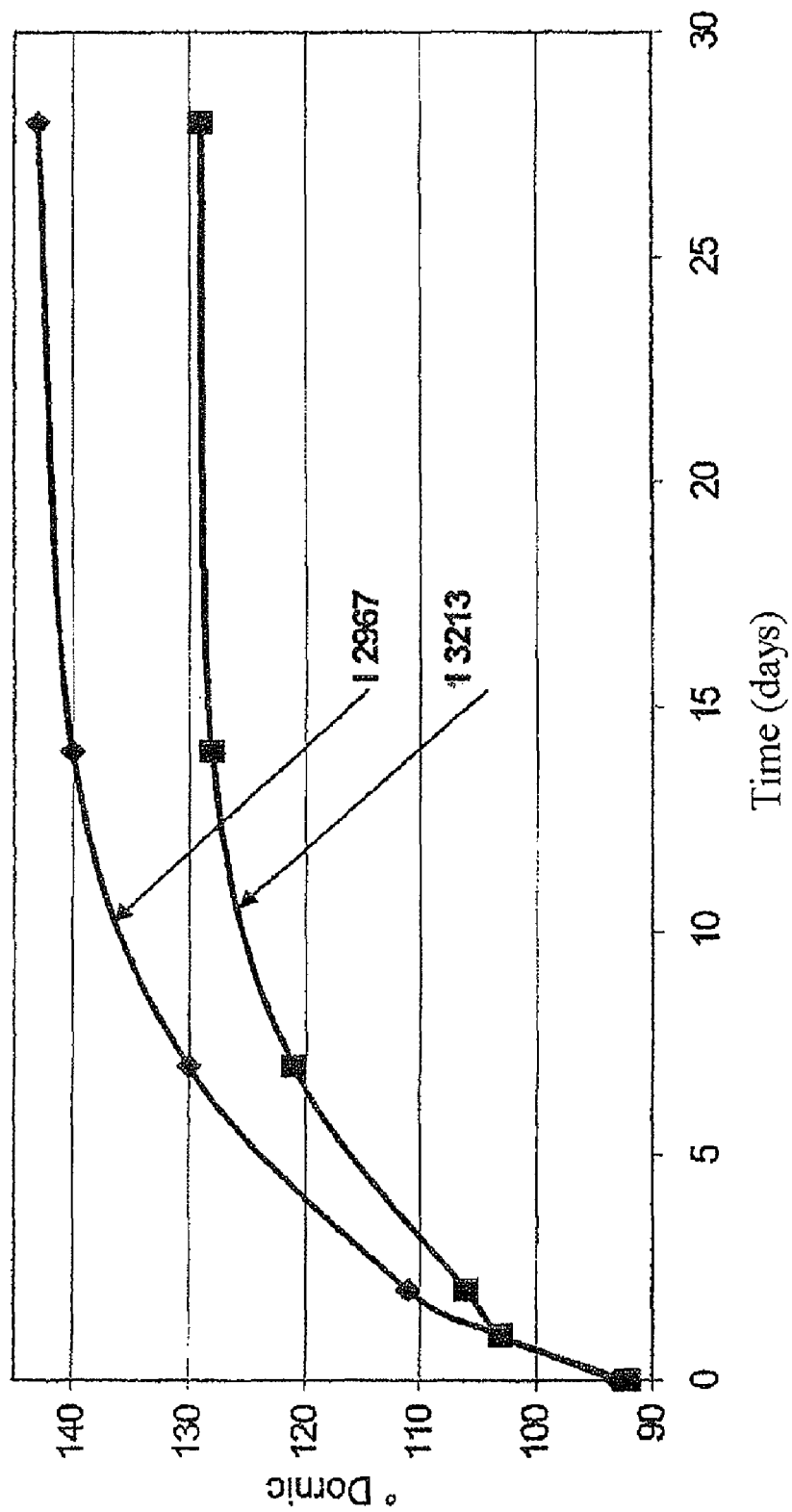
FIG. 4: Monitoring of the Dornic acidity during the storage of the products. Comparison of the I-3213 mutant and of the I-2967 parent strain.

2.C—Monitoring—Comparison of the Post-acidification of the I-3213 Mutant and the I-2967 Strain FIG. 4 shows the results of the monitoring of the Dornic acidity during storage of the products, by comparing the products obtained by fermentation with the I-3213 mutant and with the I-2967 parent strain.

The results regarding the measurement of the pH immediately after arrest of fermentation (D0) and after 28 days of storage at 10° C. are given in table 1 below.

TABLE 1

|        | pH D0 | pH D28 |
|--------|-------|--------|
| I-2967 a | 4.65  | 4.07   |
| I-2967 b | 4.64  | 4.08   |
| I-3213 a | 4.60  | 4.27   |
| I-3213 b | 4.65  | 4.19   |

All these results confirm that the mutant has a lower post-acidification than the parent strain.

2.D—Monitoring—Comparison of the Survival of the Mutants and That of I-2967

Table 2 below indicates the number of bacterial colonies present in 1 ml of product after 28 days of storage at 10° C.

TABLE 2

|        | CFU/ml D28        |
|--------|-------------------|
| I-2967 a | $1.4 \times 10^7$ |
| I-2967 b | $7.6 \times 10^7$ |
| I-3213 a | $7.4 \times 10^7$ |
| I-3213 b | $1.0 \times 10^8$ |

These results show that the survival of the mutant is as good as that of the parent strain, after 28 days of storage following the arrest of fermentation.

2.E—Monitoring—Comparison of the Texture of the Products Obtained Using a Mutant and Those Obtained Using the I-2967 Parent Strain The texture measurements were carried out on the products from a single production. All the measurements were carried out in triplicate (3 jars per measurement).

Three methods for measuring the texture were carried out on the products at D+7:
Penetrometry measurement with TAXT2 (10° C.)
Measurement of flow after manual stirring on a Rheomat 260 (4° C.)
Measurement of viscosity on the serum after centrifugation on an MCR300 (20° C.)
These various techniques for measuring texture are described in detail below.

2.E.1—Measurement of Viscosity on the Serum of the Set Products

The advantage of this method consists in analyzing the serum of the set products in order to confirm the rheological characteristics of the milks fermented by the strains.

This analytical method makes it possible, firstly, to recover the serum from the set products. For this, an amount of product, approximately 50 g, is centrifuged at 631 g for 10 minutes at ambient temperature, which makes it possible to collect the serum present inside the gel of the milks fermented by the strains. The serum is then removed and undergoes the same centrifugation in order to remove the majority of the product residues. The rest of these particles sediments to form a fragile pellet.

The viscosity of the serum is then measured at 20° C. and at a fixed shear gradient of 100 s$^{-1}$ for one minute. Three measurements are also carried out on three jars of milk fermented by the same strain and under the same conditions. The apparatus used for this analysis is an Anton Paar Physica® MCR 300 rheometer equipped with a double gap coaxial geometry of DG 26.7/TEZ 150 p-c type, and also a Peltier-effect temperature regulation system. This rotating system makes it possible to evaluate the viscosity of the serum at a constant shear rate with an acquisition of one point per second.

Generally, the first two values of this measurement are incoherent and distorted by the initialization of the rotating system. As a result, the viscosity of each serum [Vs] is determined by the mean of the values retained by the apparatus, except the first two.

2.E.2—Penetrometry Measurement (Fgel-Dgel-F15 mm)

The apparatus used for this measurement is a Thermo Rheo TAXT2 penetrometer (Anton Paar Physica, Austria).

A cylinder approximately 1 cm in diameter penetrates into the gel (tempered at 10° C.) at a constant speed to a depth of 15 mm. When the spindle descends into the product, the gel offers a resistance and it will deform before breaking. The force which results therefrom is measured.

The parameters extracted are the following:
Fgel=Gel strength (g), corresponds to the value of the force applied by the spindle at the time the gel breaks (first peak of the curve).
Dgel=Distance at the gel strength (mm), corresponds to the depth to which the spindle has penetrated at the time the gel breaks.
F15=Force at 15 mm (g), corresponds to the force measured when the spindle is at the end of its path.

2.E.3—Measurement of Flow—Flow Viscosity

This method consists in determining the viscosity of the set products, after manual stirring and incubation for 30 minutes at 4° C. Three measurements are carried out at 4° C. on three jars of milk fermented with the same strain and under the same conditions. The apparatus used for this analysis is a Mettler® RM 260 refrigerated viscosimeter equipped with a coaxial system of DIN 145 type. This rotating system makes it possible to observe destructuring of the product as a function of a linear shear gradient, i.e. a stress at a given gradient.

The results are obtained in the form of a continuous flow curve, ascending and descending ramp between 0 and 20 s$^{-1}$. The product is subjected to an increasing shear gradient of 0 to 20 s$^{-1}$ for 1 minute. This phase corresponds to the ascending ramp. It is then subjected to a decreasing shear gradient from 20 to 0 s$^{-1}$ for 1 minute, corresponding to the descending ramp.

Each descending curve is then modeled according to the Casson model:

$$\sqrt{\tau} = \sqrt{\tau_0} + \sqrt{\eta \times D}$$

τ: stress (Pa)
$\tau_0$: product flow threshold (Pa) [threshold 4]
η: product viscosity (Pa·s) [V4]
D: shear gradient (s$^{-1}$)

This Casson modeling, followed by a linear regression line on the descending part of the curve, makes it possible to pick out an important parameter, which is the viscosity of the product η, corresponding to the slope of the regression line.

Figure 5:
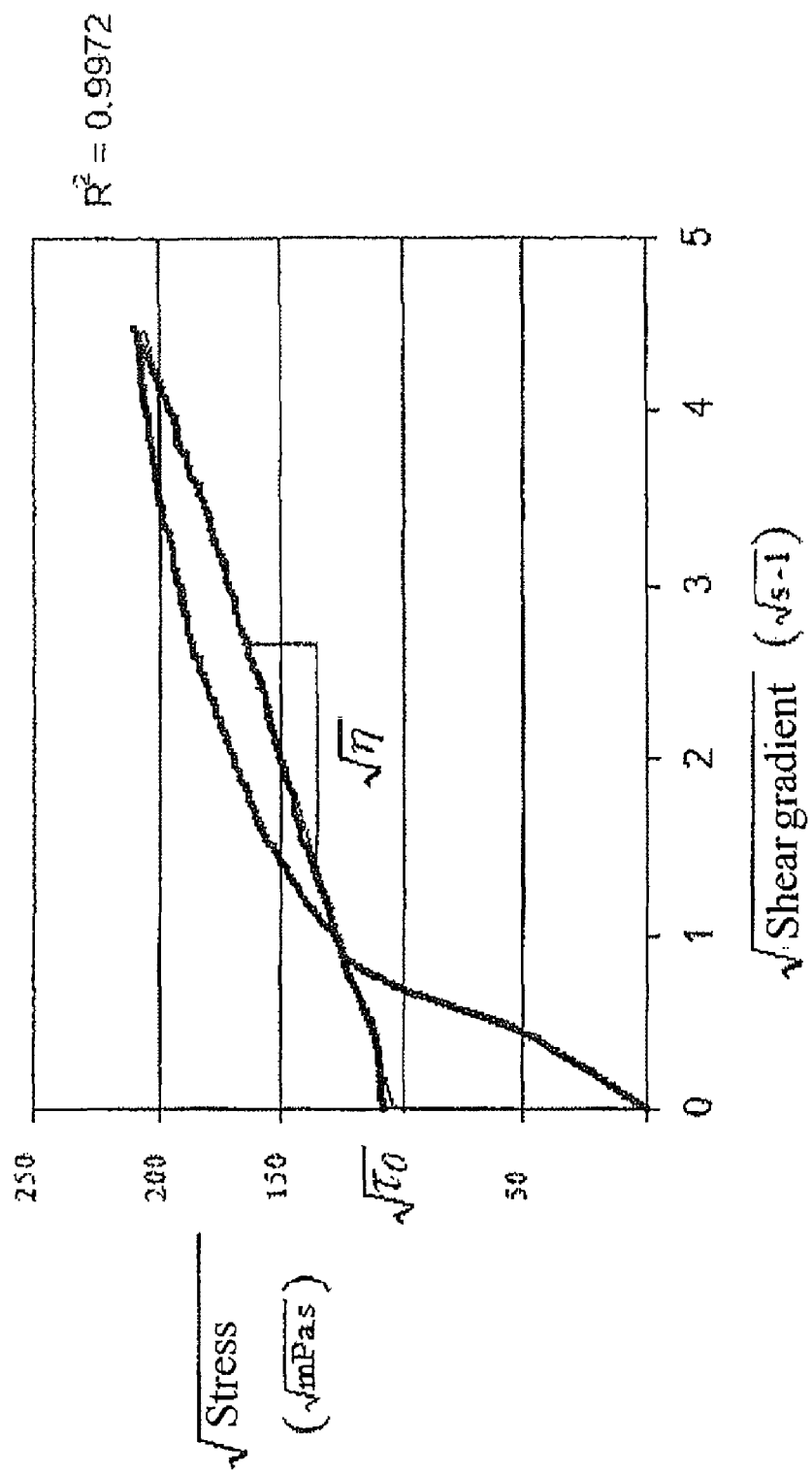
FIG. 5: Principle of the measurement of the viscosity η of a product.

FIG. 5 illustrates the method of calculating the viscosity according to this modeling.

2.E.4—Results

The results obtained with each of the measuring techniques are given in table 3 below.

TABLE 3

| Parameters modeled | I-2967 | I-3213 |
|---|---|---|
| Visco serum (mPa · s) | 2.18 | 2.31 |
| Fgel (g) | 33.58 | 33.18 |
| Dgel (mm) | 3.29 | 2.96 |
| F 15 mm (g) | 39.23 | 38.78 |
| Flow viscosity | 1154 | 1171 |

Analyses of variance (P<0.05) are carried out on the results of the texture measurements (for each parameter, the values are compared by the Student's test):
- The parameters of gel strength, distance for the gel strength and force at 15 mm show that the two strains are not significantly different.
- The viscosity parameter derived from the flow measurement shows that the two strains are not significantly different.
- The viscosity of the serum which is very reproducible shows a significant difference between the two strains, but the mutant has a much higher viscosity than the I-2967 strain, which proves that there has not been any loss of texture.

2.E.5—Interpretation

The texture measurements carried out on the fermented products obtained with the mutant and the parent strain make it possible to show that there is no loss of texture due to the mutation.

2.F—CONCLUSIONS

A non-phosphorylatable lactose permease mutant of the I-2967 strain was obtained by double recombination event. This mutant, called I-3213, has:
- an acidification curve different from that of the parent strain (rate slowed down),
- a lower post-acidification at D28,
- a texture similar to that of the parent strain, and
- good survival at D28.

REFERENCES

Biswas, I., Gruss, A., Ehrlich, S. D. and Maguin, B. (1993) High-efficiency gene inactivation and replacement system for gram-positive bacteria. *J Bacteriol*, 175, 3628-3635.

Duan, K., Liu, C. Q., Liu, Y. J., Ren, J. and Dunn, N. W. (1999) Nucleotide sequence and thermostability of pND324, a 3.6-kb plasmid from *Lactococcus lactis*. *Appl Microbiol Biotechnol*, 53, 36-42.

Frere, J., Benachour, A., Giard, J. C., Laplace, J. M., Flahaut, S. and Auffray, Y. (1998) A new theta-type thermosensitive replicon from *Lactococcus lactis* as an integration vector for *Enterococcus faecalis*. *FEMS Microbiol Lett*, 161, 107-114.

Gunnewijk, M. G. and Poolman, B. (2000a) HPr (His approximately P)-mediated phosphorylation differently affects counterflow and proton motive force-driven uptake via the lactose transport protein of *Streptococcus thermophilus*. *J Biol Chem*, 275, 34080-34085.

Gunnewijk, M. G. and Poolman, B. (2000b) Phosphorylation state of HPr determines the level of expression and the extent of phosphorylation of the lactose transport protein of *Streptococcus thermophilus*. *J Biol Chem*, 275, 34073-34079.

Jones, B. E., Dossonnet, V., Kuster, E., Hillen, W., Deutscher, J. and Klevit, R. E. (1997) Binding of the catabolite repressor protein CcpA to its DNA target is regulated by phosphorylation of its corepressor HPr. *J Biol Chem*, 272, 26530-26535.

Law, J., Buist, G., Haandrkman, A., Kok, J., Venema, G. and Leenhouts, K. (1995) A system to generate chromosomal mutations in *Lactococcus* lactis which allows fast analysis of targeted genes. *J Bacteriol*, 177, 7011-7018.

Maguin, B., Prevost, H., Ehrlich, S. D. and Gruss, A. (1996) Efficient insertional mutagenesis in lactococci and other gram-positive bacteria. *J Bacteriol*, 1.78, 931-935.

Mollet, B., Knol, J., Poolman, B., Marciset, O. and Delley, M. (1993) Directed genomic integration, gene replacement, and integrative gene expression in *Streptococcus thermophilus*. *J Bacteriol*, 175, 4315-4324.

Poolman, B., Modderman, R. and Reizer, J. (1992) Lactose transport system of *Streptococcus thermophilus*. The role of histidine residues. *J Biol Chem*, 267, 9150-9157.

van den Bogaard, P. T., Kleerebezem, M., Kuipers, O. P. and de Vos, W. M. (2000) Control of lactose transport, beta-galactosidase activity, and glycolysis by CcpA in *Streptococcus thermophilus*: evidence for carbon catabolite repression by a non-phosphoenolpyruvate-dependent phosphotransferase system sugar. *J Bacteriol*, 182, 5982-5989.

The invention claimed is:

1. A mutant lactic acid bacteria strain having a lower post-acidification than the parent strain from which it is derived, wherein said mutant strain results from the introduction into the genomic DNA of said parent strain, of a mutation of the codon encoding the HPr(His—P)-phosphorylatable histidine of the IIA domain of lactose permease, said mutation inducing the replacement of said histidine with a non-phosphorylatable amino acid, wherein the mutant strain is the mutant strain of S. thermophilus deposited on May 10, 2004, at the CNCM under number I-3213, and wherein the parent strain is a strain of Streptococcus thermophilus and in that this mutation introduces an alanine codon in place of histidine codon 552.

2. The lactic acid bacteria strain as claimed in claim 1, characterized in that it has a β-galactosidase activity.

3. A method for obtaining the mutant lactic acid bacteria strain of claim 1, characterized in that a mutation of the codon encoding the HPr(His—P)-phosphorylatable histidine of the IIA domain of lactose permease is introduced into the genomic DNA of said parent strain, said mutation inducing the replacement of said histidine with a non-phosphorylatable amino acid, and wherein the parent strain is a strain of Streptococcus thermophilus and in that this mutation introduces an alanine codon in place of histidine codon 552.

* * * * *